United States Patent
Nair et al.

(10) Patent No.: US 6,623,945 B1
(45) Date of Patent: *Sep. 23, 2003

(54) SYSTEM AND METHOD FOR MICROWAVE CELL LYSING OF SMALL SAMPLES

(75) Inventors: Vijay K. Nair, Mesa, AZ (US); Herbert Goronkin, Tempe, AZ (US)

(73) Assignee: Motorola, Inc., Schaumburg, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/397,691

(22) Filed: Sep. 16, 1999

(51) Int. Cl.$^7$ .............................................. C12N 13/00
(52) U.S. Cl. ................................. 435/173.4; 435/173.7
(58) Field of Search ........................... 435/173.4, 173.7

(56) References Cited

U.S. PATENT DOCUMENTS

| | | |
|---|---|---|
| 4,327,180 A | 4/1982 | Chen |
| 4,582,629 A | 4/1986 | Wolf |
| 4,674,325 A | 6/1987 | Kiyobe et al. |
| 4,865,748 A | 9/1989 | Morse |
| 4,866,231 A | 9/1989 | Schneider |
| 4,891,239 A | 1/1990 | Dudley et al. |
| 5,073,167 A | 12/1991 | Carr et al. |
| 5,191,182 A * | 3/1993 | Gelorme et al. ............ 219/696 |
| 5,252,294 A | 10/1993 | Kroy et al. |
| 5,304,487 A | 4/1994 | Wilding et al. |
| 5,306,887 A | 4/1994 | Smith |
| 5,403,730 A * | 4/1995 | Bayer et al. ............. 435/173.1 |
| 5,521,360 A | 5/1996 | Johnson et al. |
| 5,635,143 A | 6/1997 | White et al. |
| 5,639,423 A | 6/1997 | Northrup et al. |
| 5,690,614 A | 11/1997 | Carr et al. |
| 5,720,927 A | 2/1998 | Cripe et al. |
| 5,782,897 A | 7/1998 | Carr |
| 5,922,591 A | 7/1999 | Anderson et al. |
| 6,043,080 A | 3/2000 | Lipshutz et al. |

FOREIGN PATENT DOCUMENTS

| | | |
|---|---|---|
| WO | WO 95/15671 | 6/1995 |

OTHER PUBLICATIONS

Partlow et al. Effects of millimeter–wave radiation on monolayer cell cultures.I. design and validation of a novel exposure system (1981) Bioelectromagnetics, vol. 2, pp. 123–140.*
Ponne et al., Effect of radio frequency energy on biological membranes and microorganisms (1996) Food Science and Technology LWT, vol. 29, pp. 41–48.*
Fujikawa et al. Patterns of bacterial destruction in solutions by microwave irradiation (1994) Journal of Applied Bacteriology, vol. 76, pp. 389–394.*
Hultner et al., A bacterial plasmid DNA miniprep using microwave lysis (1994) Biotechniques, vol. 16, No. 6, pp. 990–994.*
Ghandi, "VLSI Fabrication Principles," Wiley (1983) Chapter 10.
Hurley et al., "Rapid lysis technique for mycobacterial species," 1987, J. Clin. Microbiol. 25:2227–2229.
Grimberg et al., "A simple methods for the preparation of plasmid and chromosomal E. coli DNA," 1989, Nucleic Acids Res. 17:8893.
Waters et al., "Microchip device for cell lysis, multiplex PCR amplification, and electrophoretic sizing," 1998, Anal. Chem. 70:158–162.
Whittaker, G. 1998, "Fast and Furious," New Scientist, Feb. 28, 1998, p. 34–37.
Dealler et al., "Superficial microwave heating," 1990, Nature (London) 344:496.
Hultner et al., "A Bacterial plasmid DNA miniprep using microwave lysis," 1994, Biotechniques 16:990–994.
Goodwin et al., "Microwave miniprep of total genomic DNA from fungi, plants, protists and animals for PCR," 1993, Biotechniques, 15:438–444.
Jones et al., "An oligonucleotide probe to assay lysis and DNA hybridization of a diverse set of bacteria," 1989, Anal. Chem. 181:23–27.
Bollet et al., "A simple method for the isolation of chromosomal DNA from Gram positive or acid–fast bacteria," 1991, Nucleic Acids Res. 19:1955.
Cheyrou et al., "Improved detection of HBV DNA by PCR after microwave treatment of serum," 1991, Nucleic Acids Res. 19:4006.
Jacobsen, C.S., "Microscale detection of specific bacterial DNA in soil with a magnetic capture–hybridization and PCR amplification Assay," 1995, Appl. Environm. Microbiol. 61:3347–3352.
Vogelstein et al., "Preparative and analytical purification of DNA from agarose," 1979, Proc. Natl. Acad. Sci. 76:615.
Fujikawa et al., (1992) "Kinetics of *Escherichia coli* Destruction by Microwave Irradiation." *Applied and Environmental Microbiology*. vol. 58, pp. 920–924.
S. W. Lee et al., (1998) "A Micro Cell Lysis Device" *IEEE the 11$^{th}$ International Workshop on Micro Electro Mechanical Systems, Heidelberg, Germany, Jan. 25–29, 1998.*
T. Koryu Ishii, (1995) "Chapter 8: Propagation at Microwave Frequencies" *Handbook of Microwave Technology*, vol. 2, pp. 207–227.

* cited by examiner

*Primary Examiner*—Jon P. Weber
(74) *Attorney, Agent, or Firm*—Douglas W. Gilmore

(57) ABSTRACT

Efficient cell lysis in small samples, i.e., samples less than one milliliter, is achieved by exposing the sample to microwave radiation in the frequency range of 18 to 26 GHz. The sample containing cells is supported in a wave-guide cavity, and a microwave source provides microwave radiation to the input port of the wave-guide cavity. A computer controls the frequency and source power level of the microwave radiation produced by the microwave source. The computer also monitors the input power level of the microwave radiation at the input port by means of an input power measuring instrument, the output power level at the output port by means of an output power measuring instrument, and the temperature of the sample by means of a thermocouple. In this way, the computer can control the operating parameters to achieve efficient cell lysis.

9 Claims, 2 Drawing Sheets

US 6,623,945 B1

SYSTEM AND METHOD FOR MICROWAVE CELL LYSING OF SMALL SAMPLES

BACKGROUND OF THE INVENTION

1. Field of the Invention

This invention relates to the field of microwave technology. More particularly, this invention relates to a system and method for heating small samples and for lysing small samples of cells.

2. Description of Related Art

Cell lysis is the process of breaking apart the cell membrane to release the cell contents. In many cases, the cell contents of interest are the nucleic acids, i.e., the DNA or RNA. For example, cell lysis is typically performed on cells to release the DNA or RNA as the first step in amplification processes such as PCR.

Currently, cell lysing is most commonly accomplished chemically, such as by using detergents, solvents, or enzymes. However, this approach has the disadvantage of requiring a supply of the appropriate chemicals, with the associated storage and disposal problems.

Cell lysing can also be accomplished thermally. For example, the sample can be placed in thermal contact with a thermal block, such as a hot plate. However, such conventional heating techniques often take a relatively long time, which can result in excessive evaporation of the sample.

Microwave irradiation can also be used for cell lysing. Notably, microwave cell lysing appears to be related to thermal cell lysing. In particular, it has been found that the cell lysing accomplished by microwave irradiation can be attributed primarily to thermal effects. See Hiroshi Fujikawa, "Kinetics of *Escherichia coli* Destruction by Microwave Irradiation," Applied and Environmental Microbiology, March, 1992, p. 920–24. Thus, microwave irradiation stands as a particularly convenient method for heating samples to the extent required for cell lysing. In particular, samples can typically be heated for cell lysing more quickly using microwave irradiation than by conventional heating. This allows greater speed and efficiency in the cell lysing process. Additionally, the microwave cell lysing process is typically easier to control, because the microwave radiation may be easily turned on or off as required. Thus, the possibility of excessive evaporation of the sample is reduced.

However, the benefits of microwave cell lysis are more difficult to apply to small samples, i.e., samples less than one milliliter. Conventional microwave ovens apply microwave radiation at a frequency of 2.45 GHz. This frequency is used because of FCC regulations and because high power sources at this frequency are readily available. However, the heating of small samples at this frequency is not very efficient because the dimensions of the sample are small compared to the wavelength of the microwave radiation. This is a significant difficulty because in many cases, particularly when amplification techniques are to be used, only small samples are available.

Accordingly, there is a need to provide more efficient microwave cell lysis of small samples.

SUMMARY OF THE INVENTION

In a first principal aspect, the present invention provides a system for heating a sample. The system includes a microwave heating chamber having a wave-guide cavity with an input port and an output port and means for supporting the sample in the wave-guide cavity. A microwave source producing microwave radiation at a source power level at a source frequency is coupled to the input port so as to supply microwave radiation to the input port at an input power level. The source frequency is between 18 and 26 GHz. The microwave exits the output port at an output power level.

In a second principle aspect, the present invention provides a method for heating a sample. The sample is placed in a wave-guide cavity having an input port and an output port. Microwave radiation is applied to the input port of the wave-guide cavity at an input power level at a predetermined frequency to heat the sample at a predetermined temperature for a predetermined time. The predetermined frequency is between 18 and 26 GHz. The microwave radiation exits said output port at an output power level.

In a third principal aspect, the present invention provides a method for microwave cell lysis. The sample, which includes cells, is placed in a wave-guide cavity having an input port and an output port. Microwave radiation is applied to the input port of the wave-guide cavity at an input power level at a predetermined frequency for a predetermined period of time, the predetermined period of time being sufficient for lysis of said cells. The predetermined frequency is between 18 and 26 GHz. The microwave radiation exits said output port at an output power level.

By using microwave radiation with a frequency in the range of 18 to 26 GHz the heating of small samples, and, thus, cell lysing, is much more efficient than when the conventional microwave frequency of 2.45 GHz is used.

DETAILED DESCRIPTION OF THE INVENTION

Figure 1:
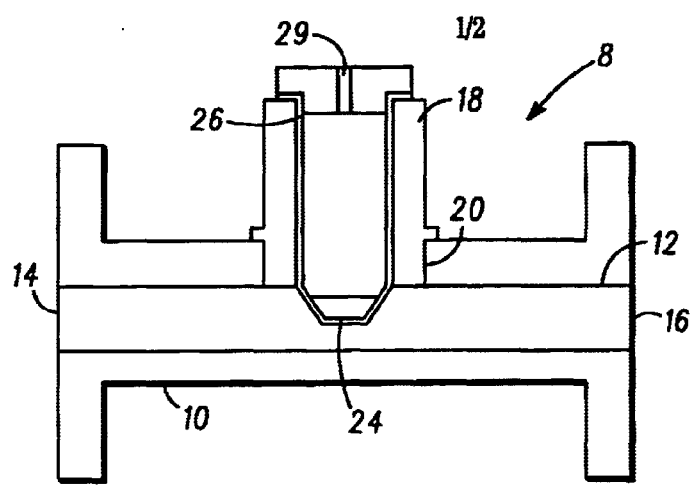
FIG. 1 is a cross-sectional view of a microwave heating assembly in accordance with a preferred embodiment of the present invention.

With reference to FIG. 1, a microwave heating assembly 8 includes a microwave heating chamber 10 that defines a wave-guide cavity 12 having an input port 14 and an output port 16. A sample holder 18 is fitted into a hole 20 formed into chamber 10. A sample 24 is contained in a vial 26, which is supported in sample holder 18 such that vial 26 extends into wave-guide cavity 12. Vial 26 is preferably made out of a material, such as polypropylene, that is substantially transparent to microwaves. In this way, microwave radiation introduced at input port 14 may be partially absorbed by sample 24, so as to heat sample 24, and then exit at output port 16. Preferably, a cap 28 is tightly fitted into the open top of vial 26 to prevent sample 24 from spilling, such as when sample 24 is heated to boiling, Cap 28 preferably includes a small hole 29, through which a thermocouple or other probe may be inserted to reach sample 24.

Figure 2:
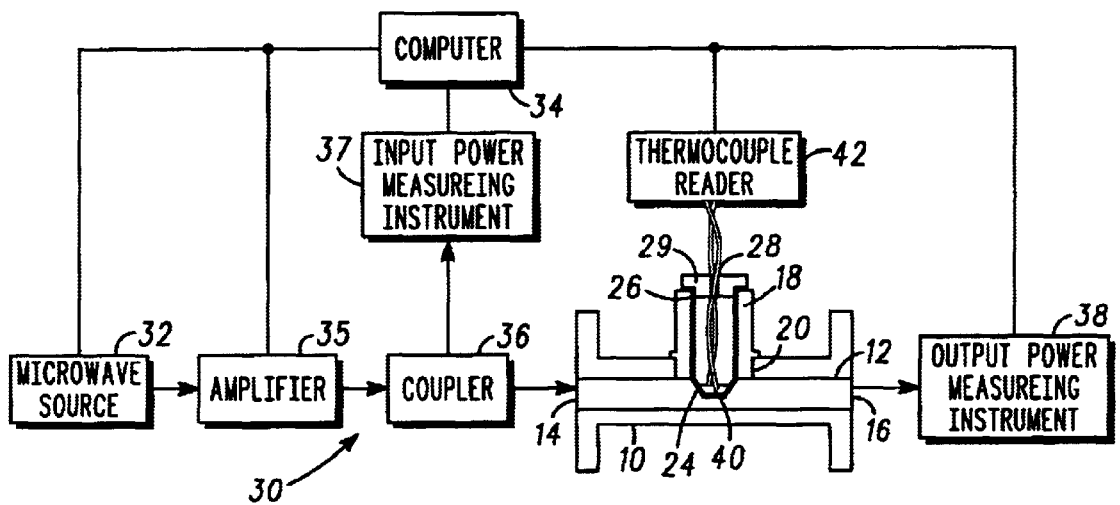
FIG. 2 is a schematic representation of a microwave heating system, which includes the microwave heating assembly of FIG. 1, in accordance with a preferred embodiment of the present invention.

Shown in FIG. 2 is a microwave heating system 30, which is particularly suited for heating small samples and for performing microwave cell lysis in small biological samples. System 30 includes microwave heating assembly 8 and further includes a microwave source 32, such as a solid state source, that can produce microwave radiation having a source frequency between 18 and 26 GHz. As discussed below, this range of frequencies has been found to be particularly efficient for heating small biological samples. Preferably, microwave source 32 is adjustable so as to allow the source frequency of the microwave radiation produced to be adjusted over the full range of 18 to 26 GHz. Preferably, the source power level of the microwave radiation produced by microwave source 32 is also adjustable. Most preferably, microwave source 32 is computer-controllable, so as to allow the source frequency and the source power level to be adjusted by a computer 34. A suitable such computer-controllable microwave source is model HP8340A sold by Hewlett-Packard Co.

The output of microwave source 32 may be coupled to an amplifier 35 to provide a desired gain. In the preferred embodiment, amplifier 35 is a traveling wave tube amplifier, such as model 8001H sold by Hughes Electronics Corp. Other types of amplifiers could also be used, however. For example, amplifier 35 may have an adjustable gain that may be controlled by computer 34.

The output of amplifier 35 is connected to a coupler 36. Coupler 36 directs most of the microwave radiation to input port 14, but coupler 36 also directs a portion of the microwave radiation to an input power measuring instrument 37. Input power measuring instrument 37 can be a spectrum analyzer, power meter, or other device that measures the power level of microwave radiation. Preferably, input power measuring instrument 37 is a spectrum analyzer that can be interfaced with computer 34. A suitable such spectrum analyzer is model HP8563E sold by Hewlett-Packard Corp. In this way, computer 34 can monitor the input power level, i.e., the power level of the microwave radiation entering wave-guide cavity 12 at input port 14. Typically, an input power level on the order of 30 dBm (1 Watt) is suitable for cell lysis when frequencies in the range of 18 to 26 GHz are used.

Preferably, the microwave radiation exiting from output port 16 is measured by an output power measuring instrument 38, which may be spectrum analyzer, power meter, or other device that can measure the power level of microwave radiation. Output power measuring instrument 38 is preferably a spectrum analyzer that can interface with computer 34, so that computer 34 can monitor the output power level, i.e., the power level of the microwave radiation exiting from output port 16.

Typically, the connections to and from microwave source 32, amplifier 35, coupler 36, input power measuring instrument 37, and output power measuring instrument 38 will be coaxial connectors having an impedance of 50 ohms. Accordingly, coaxial to wave-guide adapters (not shown) are connected to input port 14 and output port 16 to couple the microwave radiation to wave-guide channel 12. Such coaxial to wave-guide adapters are commercially available.

Preferably, a thermocouple 40 is inserted through hole 29 in cap 28 and placed in sample 24 to measure the temperature of sample 24. Thermocouple 40 is connected to a thermocouple reader 42, which measures the voltage from thermocouple 40 in comparison with either an internal or external reference to determine the sample temperature. Preferably, thermocouple reader 42 is interfaced with computer 34, so that computer 34 can monitor the sample temperature. Although thermocouples are particularly convenient, other temperature sensors, such as thermistors, or resonant tunneling diodes, could also be used.

System 30, as described above, is designed to be able to provide accurate temperature control for cell lysis and also to have the flexibility of being able to operate efficiently with a variety of different types of samples. In using system 30, it is preferable to determine, by means of input power measuring instrument 37 and output power measuring instrument 38, the power loss intrinsic to chamber 10, i.e., with no sample present, over the range of available source frequencies. Then, when sample 24 is added, thee power loss can be measured again to determine the absorptance of sample 24. Based on this absorptance, computer 34 can then set the source power level of microwave source 32 and/or the gain of amplifier 35 so that the input power level will be optimal for cell lysis.

Additionally, computer 34 can monitor the cell lysis process by measuring the sample temperature, as described above. Because microwave cell lysis appears to be correlated with heating, the cell lysis process will typically be controlled by controlling the sample temperature, the duration of a given sample temperature, and the temperature ramp rate. For example, a cell lysis operation may require that the sample be maintained at a particular temperature, such as 100° C. for a particular period of time. By monitoring the sample temperature, and by controlling the source power level of microwave source 32 and/or the gain of amplifier 35, computer 34 can control the temperature ramp rate and can maintain the sample temperature at a predetermined level for a predetermined time, for optimal cell lysis.

It has been found that by using high frequency microwave radiation, the heating of small samples, and, thus, cell lysis in small samples, is much more efficient than heating by the 2.45 GHz of conventional microwave ovens. This is believed to result from the shorter wavelength of the high frequency microwaves being more similar to the dimensions of the sample. Additionally, most samples of biological materials are composed mostly of water. It is known that pure water has a broad dipole resonance at a frequency in the vicinity of 21 GHz, depending on the phase, temperature, and the presence of impurities. Thus, the use of microwave radiation in the frequency range of 18 to 26 GHz will be particularly efficient at heating because of this resonant absorption.

Figure 3:
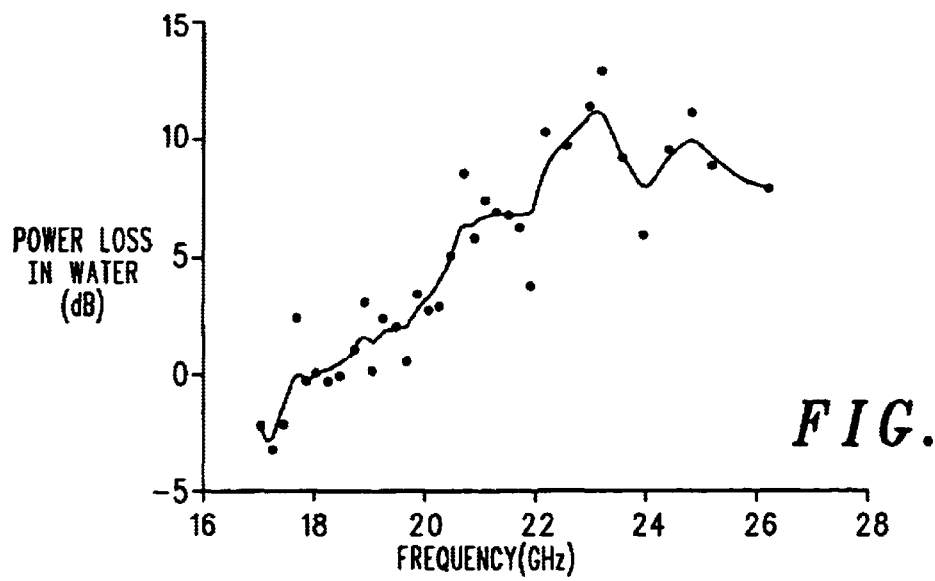
FIG. 3 is a plot of the measured power loss versus frequency for a sample of deionized water placed in the microwave heating system of FIG. 2.

In fact, measurements of the power loss in water, using microwave heating system 30, demonstrate that the absorptance of microwave radiation is beneficially high in the frequency range of 18 to 26 GHz, as shown in FIG. 3. Additionally, microwave radiation in this frequency range is useful for heating small samples because of the short wavelengths, relative to the 2.45 GHz used in conventional microwave ovens.

Figure 4:
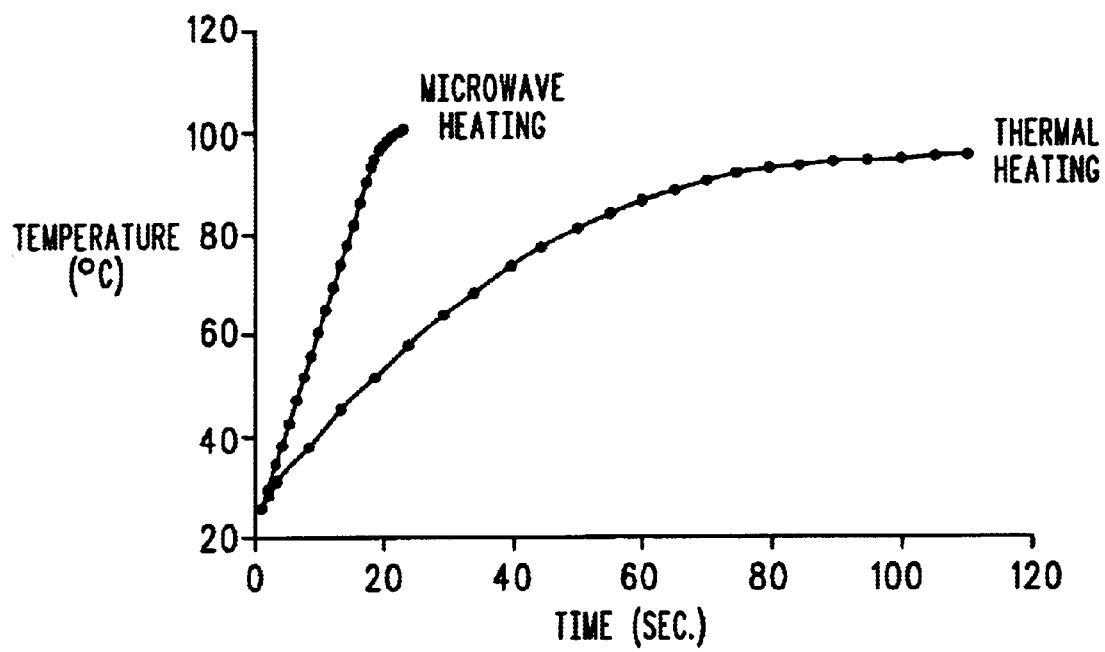
FIG. 4 is a plot comparing the temperature rise in a sample of water caused by microwave heating, using the microwave heating system of FIG. 2, with the temperature rise in the sample of water caused by heating with a thermal block.

In particular, using microwave heating system 30, it has been found that when microwave radiation in the frequency range of 20 to 22 GHz is used at an input power level of approximately 30 dBm (1 Watt), a 25 microliter sample of deionized water can be heated to its boiling point in only about 20 seconds, as shown in FIG. 4. In contrast, it was found that the same amount of sample could not be heated in a conventional microwave oven operating at 2.45 GHz and a power level of over 600 Watts.

Further, as shown in FIG. 4, even after 110 seconds of heating the 25 microliter sample using a thermal block, namely a conventional hotplate at a temperature of 120° C., the sample temperature still did not reach 100° C.

Figure 5:
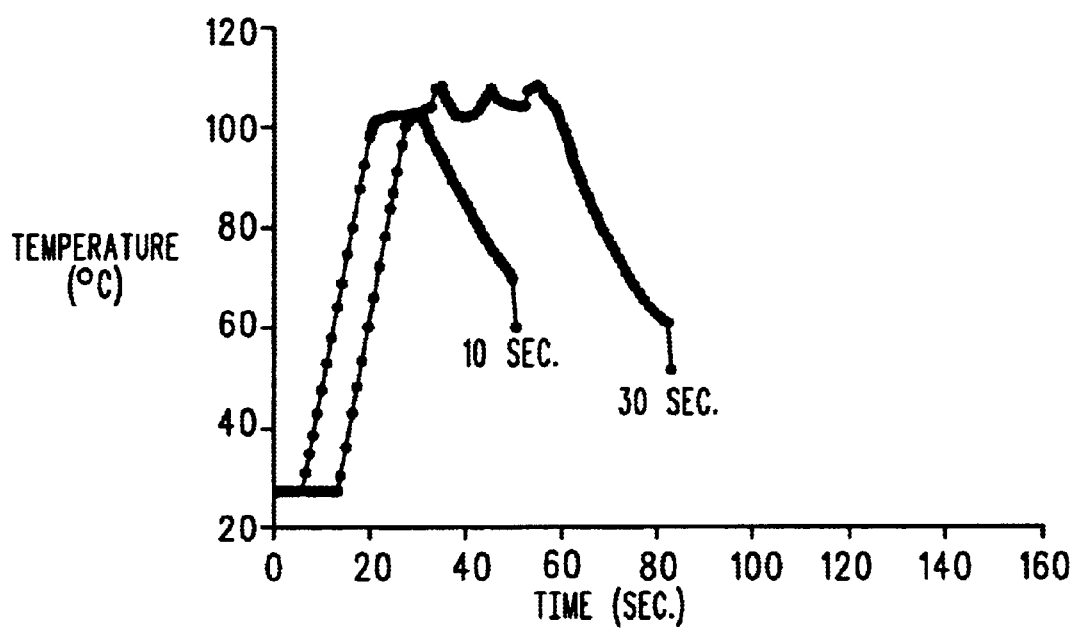
FIG. 5 is a plot of the temperature rise in a sample of *E. coli* caused by microwave heating, using the microwave heating system of FIG. 2.

The results for deionized water have been found also to apply to biological samples, indicating that the technique is useful for microwave cell lysis. In particular, as shown in FIG. 5, when using microwave radiation with a frequency of 22 GHz and a power level of 29.7 dBm, a 25 microliter sample of *E. coli* was also able to be heated from room temperature to 100° C. in about 20 seconds. FIG. 5 shows two plots: one in which the 100° C. temperature was maintained for 10 seconds and another plot in which the temperature was maintained for 30 seconds.

With the importance of the frequency of the microwave radiation, it may be desirable to measure the absorptance of a sample or of a run of samples, in order to determine the optimal frequency for cell lysis. This process may be done automatically by computer 34 controlling the source frequency of microwave source 32. In this way, system: 30 may take full advantage of the enhancement in cell lysis efficiency that is afforded by high frequency microwave radiation, relative to 2.45 GHz radiation.

In addition to the resonance at approximately 21 GHz, other water resonances exist at even higher microwave frequencies. For example, water vapor also has resonances at approximately 190 GHz and at approximately 310 GHz. However, taking advantage of these higher frequency resonances is more difficult for at least two reasons. First, it is difficult and costly to achieve power levels of even 1 Watt at these higher microwave frequencies. Second, because the dimensions of a wave-guide cavity are inversely proportionally to the frequency, these higher frequency resonances would require very small wave-guide dimensions. Such small dimensions would make the construction of a three-dimensional wave-guide cavity, such as provided in chamber 10, more difficult. Additionally, such small wave-guide cavities would not be able to accommodate conventional sample vials, as does chamber 10 of the present invention. It may be possible, however, to construct wave-guide cavities having the required dimensions using more sophisticated techniques. For example, a two-dimensional wave-guide might be fabricated in an appropriate substrate material. Accordingly, the frequency range of 18 to 26 GHz is particularly beneficial in being able to take advantage of a microwave water resonance using a wave-guide that is easy to construct and using microwave power sources and amplifiers that are readily available.

Although an exemplary embodiment has been illustrated and described, it is to be understood that changes and modifications may be made to the invention without departing from the spirit and scope of the invention, as defined by the following claims.

We claim:

1. A method for microwave assisted cell lysis, said method comprising the steps of:

providing a sample, said sample including at least a plurality of cells, the volume of said sample comprising up to about 1 mL;

providing microwave radiation comprising at least one of a predetermined frequency, a predetermined wavelength and a predetermined intensity;

placing said sample a wave-guide cavity, said wave-guide cavity having an input port and an output port the dimensions of said wave-guide cavity suitably adapted for effective transmission of microwave radiation in the range of about 18 to about 26 GHz, and applying to said input of said wave-guide cavity said microwave radiation at an input power level of said predetermined frequency for a predetermined period of time, said predetermined frequency in the range of about 18 to about 26 GHz, said microwave radiation exiting said output port at an output power level, said predetermined period of time being sufficient for lysis of at least a portion of said cells.

2. The method of claim 1, further comprising the step of measuring the temperature of said sample substantially during exposure to said microwave radiation.

3. The method of claim 2, wherein the sample temperature is measured with a thermocouple.

4. The method claim 1, further comprising the step of measuring at least one of said input power level and said output power level.

5. The method of claim 4, further comprising the step of adjusting at least one of said predetermined frequency and said input power level as a function of said output power level.

6. The method of claim 1, wherein said sample is effectively contained in a vial and at least a portion of said vial remains substantially outside said wave-guide cavity.

7. The method of claim 1, further comprising the steps of:

determining the intrinsic power loss of said cavity; and determining the absorptance of said sample.

8. The method of claim 1, further comprising the steps of:

measuring said input power level, said output power level and the temperature of said sample; and adjusting at least one of said input power level and said predetermined frequency as a function of at least one of said input power level, said output power level and the temperature of said sample.

9. The method of claim 8, wherein said step of adjusting is performed substantially automatically by a processor.

* * * * *